United States Patent [19]

Brenner et al.

[11] Patent Number: 4,816,606

[45] Date of Patent: Mar. 28, 1989

[54] CONTINUOUS PREPARATION OF ALDEHYDES AND KETONES

[75] Inventors: Karl Brenner, Ludwigshafen; Manfred Eggersdorfer, Frankenthal; Wilhelm Ruppel, Schwetzingen; Harald Schultheiss, Frankenthal; Hans-Ulrich Scholz, Weisenheim, all of Fed. Rep. of Germany

[73] Assignee: Basf Aktiengesellschaft, Ludwigshafen, Fed. Rep. of Germany

[21] Appl. No.: 103,439

[22] Filed: Sep. 30, 1987

[30] Foreign Application Priority Data

Oct. 4, 1986 [DE] Fed. Rep. of Germany .... 3633885

[51] Int. Cl.$^4$ ............................................. C07C 45/39
[52] U.S. Cl. ..................... 568/402; 568/320; 568/360; 568/471; 568/473; 568/431
[58] Field of Search ............... 568/402, 320, 360, 471, 568/404, 473, 431

[56] References Cited

U.S. PATENT DOCUMENTS

| | | | |
|---|---|---|---|
| 2,042,220 | 5/1936 | Groll et al. | 568/402 |
| 2,464,244 | 3/1949 | Levine et al. | 568/402 |
| 3,778,477 | 12/1973 | Mueller et al. | 568/402 |
| 3,894,916 | 7/1975 | Fischer et al. | 568/402 |
| 4,110,403 | 8/1978 | Ichikawa | 568/402 |
| 4,154,762 | 5/1979 | Huang et al. | 568/402 |
| 4,165,342 | 8/1979 | Dudeck et al. | 568/402 |
| 4,359,587 | 11/1982 | Abdurakhmanor et al. | 568/403 |
| 4,474,996 | 10/1984 | Carcia et al. | 568/471 |

FOREIGN PATENT DOCUMENTS

| | | | |
|---|---|---|---|
| 0055354 | 10/1981 | European Pat. Off. | 568/402 |
| 2243810 | 10/1973 | Fed. Rep. of Germany | 568/402 |
| 2020865 | 6/1975 | Fed. Rep. of Germany | 568/402 |
| 2517859 | 3/1976 | Fed. Rep. of Germany | 568/402 |
| 2041976 | 6/1979 | Fed. Rep. of Germany | 568/402 |
| 2715209 | 8/1980 | Fed. Rep. of Germany | 568/402 |
| 2231650 | 12/1974 | France | 568/402 |
| 59-933 | of 1983 | Japan | 568/402 |
| 246340 | of 1985 | Japan | 568/402 |
| 960160 | 9/1982 | U.S.S.R. | 568/402 |

Primary Examiner—James H. Reamer
Attorney, Agent, or Firm—John H. Shurtleff

[57] ABSTRACT

Aldehydes and ketones of the general formula I $$R^1-\overset{O}{\underset{\|}{C}}-R^2 \quad (I)$$

where $R^1$ is hydrogen or an organic radical of 1 to n carbon atoms and $R^2$ is a non-aromatic organic radical of 1 to m carbon atoms, (m+n) ranging from 2 to 24 and $R^1$ and $R^2$ being combinable to form a 4- to 12-membered ring, are prepared in a continuous manner by oxidizing an alcohol of the general formula II $$R^1-\underset{\underset{H}{|}}{\overset{OH}{\underset{|}{C}}}-R^2 \quad (II)$$

with oxygen or an oxygen-containing gas at elevated temperatures in the gas phase in the presence of a catalyst, by effecting the oxidation by means of a supported catalyst composed of an inert carrier having a smooth surface and from 0.1 to 20% by weight, based on the amount of carrier, of an active layer of copper, silver and/or gold in a tubular reactor or tube bundle reactor where the internal diameter D of the tube or tubes ranges from 10 to 50 mm and the largest diameter d of the coated supported catalysts is subject to the relationship d=from 0.1 to 0.2 D.

14 Claims, No Drawings

CONTINUOUS PREPARATION OF ALDEHYDES AND KETONES

The present invention relates to a novel process for the continuous preparation of an aldehyde or ketone of the general formula I

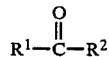

where $R^1$ is hydrogen or an organic radical of 1 to n carbon atoms and $R^2$ is a non-aromatic organic radical of 1 to m carbon atoms, (m+n) ranging from 2 to 24 and $R^1$ and $R^2$ being combinable to form a 4- to 12-membered ring, by oxidizing an alcohol of the general formula II

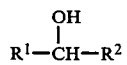

with oxygen or an oxygen-containing gas at elevated temperatures in the gas phase in the presence of a catalyst.

It is known from U.S. Pat. No. 2,042,220 that 3-methyl-3-buten-1-ol can be oxidized with an excess of oxygen at from 360° to 550° C. in the presence of metal catalysts, for example copper and silver catalysts, to 3-methyl-3-buten-1-al. The catalysts can be alloys, metal compounds or elemental metal. Preference is given to activated catalysts; the activating operations specified comprise surface amalgamation of the metal and subsequent heating of the metal surface. The preparation of copper and silver catalysts in the examples consists in reducing copper oxide particles at 300° C. under hydrogen, or in amalgamating and heating silver wire networks. It is also known from DE-B No. 2,041,976 that the known process gives rise to appreciable amounts of undesirable byproducts.

DE-A No. 2,517,859 describes the dehydrogenation of unsaturated alcohols over a copper catalyst which has a specific surface area of from 0.01 to 1.5 m²/g, substantially in the absence of oxygen at from 150° to 300° C. If the starting materials are β,γ-unsaturated alcohols, the by-products formed are α,β-unsaturated aldehydes and saturated aldehydes; the selectivity for α,γ-unsaturated aldehydes is low (page 2, last paragraph). Mixtures of this type need to be separated into their components in expensive operations.

DE-B Nos. 2,020,865 and 2,041,976 describe the dehydrogenation of β,γ-unsaturated alcohols or α,β-unsaturated alcohols to α,β-unsaturated aldehydes. The dehydrogenation catalysts mentioned also include mixed catalysts, for example those made of copper and silver. It is a disadvantage, however, that appreciable amounts of nucleophilic substances need to be added. In the case of conversion of 3-methyl-3-buten-1-ol, satisfactory results are only obtained with incomplete conversions, which, according to DE-B No. 2,243,810, leads to difficulties in separating off the unconverted starting material.

Dehydrogenation of 3-methyl-3-buten-1-ol by the method of DE-B No. 2,517,859 over metallic copper in the absence of oxygen produces appreciable amounts of isovaleraldehyde, and the activity of the catalysts decreases rapidly within a few days, so that frequent regeneration is necessary.

FR-A No. 2,231,650 describes the preparation of aldehydes and ketones from the corresponding alcohols by air oxidation at 250°–600° C. in the presence of a gold catalyst. The advantage of a gold catalyst is the higher selectivity compared with copper and silver catalysts, so that byproduct formation is reduced. The disadvantage with this process is the expensive catalyst, since a solid gold catalyst is used.

DE-B No. 2,715,209 and EP No. B-55,354 describe the oxidative dehydrogenation of 3-alkyl-buten-1-ols in the presence of molecular oxygen over catalysts which consist of layers of silver and/or copper crystals. The amount of oxygen ranges from 0.3 to 0.7 mole per mole of starting material. The disadvantage with this process is that catalyst expenses are high, because solid silver is used, and high selectivities can only be obtained if defined catalyst particle sizes or particle size distributions are used in a layer structure, even in some instances requiring specific mixtures of layers of copper and silver crystals. As a consequence, not only is the reactor expensive to charge but the catalyst is expensive to recover. In addition, the high reaction temperatures employed in this process cause sintering of the metal crystals, which leads to a pressure increase and short times-on-stream.

JP-A No. 60/246,340 describes the gas phase oxidation of 3-methyl-2-buten-1-ol to 3-methyl-2-buten-1-al at 300°–600° C. in the presence of oxygen over a supported catalyst. The supported catalyst has to be prepared in a complicated manner by impregnating the carrier with aqueous solutions of $AgNO_2$, $Cu(NO_3)_2 \times 3H_2O$ and $Mg(NO_3)_2 \times 6 H_2O$, drying, calcining within a certain temperature range and activating under hydrogen. It is true that the catalyst gives a high selectivity of 96.6%, but only at the price of a low conversion, so that this catalyst is not a realistic option for use in industry.

JP-A No. 58/059,933 describes the preparation of aldehydes and ketones by oxidative dehydrogenation of alcohols in the presence of a silver catalyst which additionally contains phosphorus. To maintain the selectivity of the reaction, a phosphorus compound is additionally introduced into the alcohol stream, so that product contamination is inevitable. Given that the aldehydes are used for scents and vitamins, the addition of an organophosphorus compound is evidently undesirable.

Since all these known processes for preparing aldehydes and ketones are unsatisfactory in respect of simplicity and economy of operation, catalyst life and purity of reactor output, it is an object of the present invention to eliminate these disadvantages.

We have found that this object is achieved with a process for the continuous preparation of an aldehyde or ketone of the general formula I

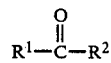

where $R^1$ is hydrogen or an organic radical of 1 to n carbon atoms and $R^2$ is a non-aromatic organic radical of 1 to m carbon atoms, (m+n) ranging from 2 to 24 and $R^1$ and $R^2$ being combinable to form a 4- to 12-membered ring, by oxidizing an alcohol of the general formula II

with oxygen or an oxygen-containing gas at elevated temperatures in the gas phase in the presence of a catalyst, which comprises effecting the oxidation by means of a supported catalyst composed of an inert carrier having a smooth surface and from 0.1 to 20% by weight, based on the amount of carrier, of an active layer of copper, silver and/or gold in a tubular reactor or tube bundle reactor where the internal diameter D of the tube or tubes ranges from 10 to 50 mm and the largest diameter d of the coated supported catalysts is subject to the relationship d=from 0.1 to 0.2 D.

If desired, the catalyst can also be diluted with an inert material without an active coating. Suitable inert materials, which are also suitable for use as carrier materials, are ceramics, such as aluminum oxide, silicon dioxide, magnesium oxide, silicon carbide and in particular steatite. However, a catalyst layer should contain not less than 10% of particles of active material.

Suitable inert shapes for the catalyst are primarily spheres and other structures such as ellipsoids, cylinders or rings. The diameter d of the spheres, or the largest diameter of the other shapes, can range from 1 to 10 mm the diameters being subject, as defined, to the relationship with the internal diameter of the reactor tubes.

The active catalyst metal is preferably applied to the inert material by flame spraying, but it is also possible to use other methods, for example impregnating or plasma spraying, provided the coating produced is abrasion-resistant; it should also be very smooth.

Compared with the prior art, the process according to the invention surprisingly produces, in a simpler and more economical manner, a better overall result in terms of yield, space-time yield and purity of end product. In particular, the amount of product relative to the catalyst used is very much larger, so that using the selective noble metal catalysts silver or even gold can result in an economical process. The catalyst is simple to prepare and, especially if of spherical shape, simple to introduce into the reactor. A further advantage of the regular shape of the catalyst is that, without further measures, an ordered, relatively close packing is obtained in the reactor and, in the case of tube bundle reactors, the uniform packing produces a similar pressure loss in every individual tube. Since the pressure loss is the same in the many tubes of a tube bundle reactor, the flow through the individual tubes is the same, which evidently leads to a substantial improvement in the selectivity of the reaction. In the course of the reaction, no one tube is put under more stress than any other, so that the catalyst life is very long, amounting in practice to several months.

The process is carried out by converting alcohol II into the gas phase and passing this gas together with oxygen over the catalyst at from 300° to 600° C., preferably at from 350° to 450° C.

The oxidizing agent used can be not only pure oxygen but also a gas containing free oxygen, in particular air. Oxygen and alcohol II are expediently used in a molar ratio of from 0.2 to 0.6, in particular from 0.3 to 0.5, mole of oxygen per mole of alcohol. If desired, it is possible to employ a solvent which is inert under the reaction conditions, for example water or ether. It is an advantage of the process according to the invention that, in addition to the nitrogen contained in the air, there is no need to use any further inert gas. Compared with the prior art processes, this results in a reduction in the inert gas content and hence in a simplification of the workup, since the useful product can be condensed from a smaller total gas stream.

Preference is given to using a tube bundle reactor of from 100 to 10,000 tubes of from 10 to 30 cm in length. For experimental purposes, it is sufficient to use just one tube.

Expediently, the catalyst is operated at a space velocity of from 0.5 to 4 tonnes, in particular from 0.7 to 2 tonnes of starting material II per m2 of catalyst bed cross-section per hour.

The reaction mixture is worked up in a conventional manner. For example, the hot reaction gas is absorbed with a solvent such as water or dimethylformamide or preferably in the condensed product mixture.

The starting compound can in principle be any desired primary alcohol II. Or it can be any desired secondary alcohol, unless both $R^1$ and $R^2$ are aromatic. $R^1$ and $R^2$ can in turn have inert substituents such as fluorine, chlorine, bromine, cyano or tertiary amino and be interrupted by oxygen or oxygen-containing groups such as —CO— and —O—CO—.

Examples are:

saturated aliphatic primary alcohols of 1 to 24, preferably 6 to 18, carbon atoms, suitable being in the main branched alcohols and ether alcohols such as 2-ethoxy-ethanol;

in particular preferably unsaturated aliohatic primary alcohols of 3 to 24, preferably 4 to 12, carbon atoms where the double bond or bonds are not in the 1,2-position, e.g.

but-2-enol
but-3-enol
pent-3-enol
pent-4-enol
hex-3-enol
hex-4-enol
hex-5-enol
hept-3-enol
hept-4-enol
hept-5-enol
oct-4-enol
oct-5-enol and in particular the $C_1$-$C_4$-alkyl homologs, in particular the methyl homologs, of these alcohols, of which in particular the butenols IIa and IIb

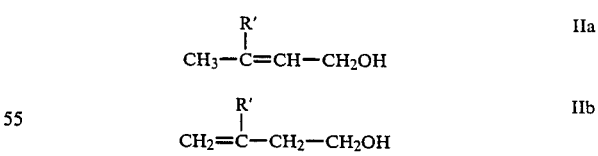

where R' is $C_1$-$C_4$-alkyl, in particular methyl. In general, the process is suitable in particular for alk-2-enols, since a group with —CH=CH—(C=O)— conjugation forms, which energywise favors the dehydrogenation;

cycloaliphatic/aliphatic primary alcohols such as hydroxymethylcyclohexane, hydroxymethylcyclohex-1-ene and the hydroxymethyltetrahydrofurans;

araliphatic primary alcohols such as 2-phenylethanol;

secondary aliphatic alcohols of 3 to 24, preferably 4 to 12, carbon atoms, for example butan-2-ol
methylbutan-2-ol but-3-en-2-ol
methylbut-3-en-2-ol
pentan-2-ol
pent-3-en-2-ol
pent-4-en-2-ol
pentan-3-ol
pent-1-en-3-ol
secondary araliphatic alcohols such as 1-phenylethanol, 1-phenylpropanol and 1-phenylprop-2-enol;
cyclic secondary alcohols, in particular those of 5 or 6 ring members, such as cyclohexanol, 3-hydroxytetrahydrofuran, 3-hydroxytetrahydropyran and 4-hydroxytetra-hydropyran.

The alcohols II are either known or obtainable by known methods.

The carbonyl compounds I preparable by the process of the invention are useful starting materials for the preparation of dyes, pesticides, pharmaceuticals, plastics, scents, such as citral, vitamins, such as vitamins A and E, and chrysanthemumcarboxylic acid.

The novel process is highly economical. In general it permits space velocities of from 50 to 500 moles per hour per liter of catalyst volume.

Preparation of catalyst 0.5 l of steatite spheres ranging from 1.6 to 2.0 mm in diameter was introduced into an open rotary drum and coated with silver powder 16 micrometers in particle size by the method of flame spraying. This comprised introducing the silver powder into an oxygen/acetylene flame and transporting it with the flame gases in partially molten form onto the carrier. The powder quantity was dimensioned in such a way that the completed catalyst contained about 4% by weight of silver, based on the total weight.

During the coating step, the carrier was tumbled in the rotary drum at a rate of 30 revolutions per minute.

The temperature in the material to be coated was about 600° C., and the coating took about 30 minutes.

The flame spraying process produced catalyst spheres having a continuous smooth and non-porous coating of metallic silver.

EXAMPLE 1

Preparation of 3-methyl-3-but-3-enal using a silver catalyst 11 ml of the catalyst were introduced into a reactor tube of 10 cm in length and 13 mm in internal diameter. A mixture of 30.1 l[S.T.P.]/h of technicalgrade 3-methyl-3-buten-1-ol (water content around 12–15% by weight) and 45.9 l[S.T.P.]/h of air was then passed through the tube at 390° C. and under 1.1 bar. The amount of oxygen in the mixture was 0.32 mole per mole of 3-methyl-3-butenol. The reaction gases were collected and analysed. The alcohol conversion was 73% and the selectivity 89%; this result did not change in the course of the test period of 10 days.

EXAMPLE 2

Preparation of 3-methylbut-3-enal using a copper catalyst 50 ml of a catalyst (steatite spheres 3.5–4.5 mm in diameter, layer of copper with a weight proportion of 9.57%, based on the inert material) which had been prepared in the same way as the silver catalyst were charged in a reactor tube 22 mm in internal diameter and 20 cm in length with a mixture of 27.7 l[S.T.P.]/h of 3-methyl-3-buten-1-ol and 75 l[S.T.P.]/h of air at a reaction temperature of 390° C. and under a pressure of 1.1 bar. The reaction products were trapped out of a bleed stream of the reaction gas, and analysed. A conversion of 78.6% and an aldehyde selectivity of 78.1% were found.

Formaldehyde and acids were only produced in trace amounts. These results were obtained after the catalyst had been operated for a total of 9 days. No loss in activity or selectivity was found even after 4 weeks on stream.

EXAMPLE 3

Preparation of oct-1-en-3-one using a silver catalyst

Example 1 was repeated, reacting 22.5 l[S.T.P.]/h of oct-1-en-3-ol and 45.2 l[S.T.P.]/h of air at 380° C. The alcohol conversion was 90% and the selectivity for the ketone 82%.

We claim:

1. A process for the continous preparation of an aldehyde or ketone of the formula

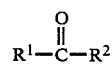

where $R^1$ is hydrogen, alkyl of 1 to 2 carbon atoms or a vinyl radical, such that when $R^1$ is hydrogen, $R^2$ is alkyl of 1 to 23 carbon atoms, an olefinically unsaturated aliphatic radical of 3 to 23 carbon atoms, 2-ethoxymethylene, cyclohexyl, cyclohex-1-enyl or benzyl, and such that when $R^1$ is alkyl of 1 to 2 carbon atoms or a vinyl radical, $R^2$ is alkyl of 1 to 22 carbon atoms, an olefinically unsaturated aliphatic radical of 3 carbon atoms or phenyl, with the proviso that the ketone contains not more than 24 carbon atoms, and where $R^1$ and $R^2$ may also be combined to form an aliphatic ring with a total of six carbon atoms, which process comprises:

oxidizing an alcohol of the formula

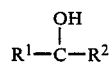

where $R^1$ and $R^2$ have the same meaning given above, at a temperature of from 300° to 600° C. in the gas phase and in contact with the supported catalyst at a space velocity of from 0.5 to 4 tons of the alcohol II per square meter of catalyst bed cross-section per hour, using oxygen in a molar ratio of from 0.2 to 0.6 moles of oxygen per mole of alcohol II, said catalyst consisting essentially of an inert carrier in the form of substantially spherically shaped particles having a smooth and non-porous surface coating supported thereon of an active layer of from 0.1 to 20% by weight, based on the amount of carrier, of at least one metal selected from the group consisting of copper, silver and gold, the catalyst being contained in a tubular or tube bundle reactor where the internal diameter D of each tube ranges from 10 to 50 mm and the diameter d of the spherically shaped carrier with its coated active layer conforms to the relationship d=from 0.1 to 0.2 D.

2. A process as claimed in claim 1, wherein the catalyst carrier material has a spherical shape.

3. A process as claimed in claim 1, wherein the carrier material is made of steatite.

4. A process as claimed in claim 1, wherein the active material of the supported catalyst is made of copper or silver.

5. A process as claimed in claim 1, wherein the oxidation is carried out at from 350° to 450° C.

6. A process as claimed in claim 1, which is applied to the oxidation of an alcohol of the general formula IIa or IIb.

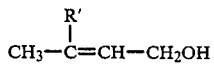 II

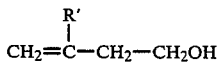 IIb where R' is $C_1$–$C_4$-alkyl.

7. A process as claimed in claim 1 wherein the alcohol II is a 1-alkenol of 4 to 12 carbon atoms or its methyl-substituted homolog in which the double bond is not in the 1,2-position.

8. A process as claimed in claim 1 wherein the alcohol II is 3-methyl-3-buten-1-ol.

9. A process as claimed in claim 1 wherein the alcohol II is oct-1-en-3-ol.

10. A process as claimed in claim 1 wherein the oxidation is carried out in a tube bundle reactor of from 100 to 10,000 tubes having a length of from 10 to 30 cm.

11. A process as claimed in claim 1 wherein the space velocity is from 0.7 to 2 tons of alcohol II per square meter of catalyst bed cross-section per hour.

12. A process as claimed in claim 1 wherein the oxidation is carried out in a tube bundle reactor using steatite spheres as the carrier material.

13. A process as claimed in claim 12 wherein the steatite spheres are surface coated with at least on metal selected from the group consisting of copper, silver or gold.

14. A process as claimed in claim 13 wherein the catalyst is diluted with up to 90% of spherical particles of an inert carrier material free of any catalyst.

* * * * *